US00PP18359P2

(12) United States Plant Patent
Parham

(10) Patent No.: US PP18,359 P2
(45) Date of Patent: Dec. 25, 2007

(54) ***CHRYSANTHEMUM* PLANT NAMED 'LETITIA TIME IMPROVED'**

(50) Latin Name: *Chrysanthemum morifolium*
Varietal Denomination: Letitia Time Improved

(75) Inventor: Ruth Parham, Bognor Regis (GB)

(73) Assignee: Cleangro Ltd., Chichester, West Sussex (GB)

( * ) Notice: Subject to any disclaimer, the term of this patent is extended or adjusted under 35 U.S.C. 154(b) by 0 days.

(21) Appl. No.: 11/494,173

(22) Filed: Jul. 27, 2006

Related U.S. Application Data

(60) Provisional application No. 60/703,358, filed on Jul. 28, 2005.

(51) Int. Cl.
*A01H 5/00* (2006.01)

(52) U.S. Cl. ..... Plt./294

(58) Field of Classification Search ..... Plt./294
See application file for complete search history.

(56) References Cited

U.S. PATENT DOCUMENTS

| | | | | |
|---|---|---|---|---|
| PP9,416 | P | 1/1996 | Hesse | Plt./82.1 |
| 2002/0129416 | P1 | 9/2002 | Boeder | Plt./294 |

OTHER PUBLICATIONS

2003 Cleangro Brochure listing the Chrysanthemun variety 'Cool Time' with a photograph at p. 7. Brochure was published Sep. 17, 2002.

2004 Cleangro Brochure listing the Chrysanthemun variety 'Cool Time' with a photograph at p. 7. Brochure was published Sep. 1, 2003.

Van Zanten North America Pot Chrysanthemun Catalog 2002 listing the Chrysanthemum varieties 'Cool Time' and 'Icey Isle' at p. 6 with photographs at p. 4. Catalog published Sep. 28, 2001.

Royal Van Zanten Catalog 2003 listing the Chrysanthemum varieties 'Cool Time' and 'Icey Isle' at pp. 45–46 and 59, with photographs at p. 30. Catalog distributed Jan. 2, 2003.

1999 Ficor Catalogue listing the Chrysanthemum varieties 'Swell Time' and 'Cool Time' as new variety introductions at pp. 4 and 12. See the photograph of 'Swell Time' at p. 2. Catalogue published Oct. 30, 1998.

2000 Ficor Catalogue listing the Chrysanthemum varieties 'Swell Time' and 'Cool Time' at pp. 4 and 12. Catalogue published Nov. 9, 1999.

*Primary Examiner*—Kent Bell
*Assistant Examiner*—S. B. McCormick-Ewoldt
(74) *Attorney, Agent, or Firm*—Winston & Strawn, LLP

(57) ABSTRACT

A new variety of *Chrysanthemum* plant named 'Letitia Time Improved', having creamy yellow buds and large cream white single flowers with a strong green disc.

1 Drawing Sheet

Latin name of the genus and species: Botanical classification: *Chrysanthemum morifolium.*

Variety denomination: The new *Chrsyanthemum* variety denomination is 'Letitia Time Improved'.

BACKGROUND OF THE INVENTION

The present invention comprises a new and distinct cultivar of *Chrysanthemum* botanically known as *Chrysanthemum morifolium,* and referred to by the cultivar name 'Letitia Time Improved'.

'Letitia Time Improved', identified as 22082-0 originated from a cross made in a controlled breeding program in Chichester, West Sussex, United Kingdom.

The female parent of the new variety is 'Swell Time', an unpatented variety and the male parent is the variety known as 'Cool Time' (U.S. Plant patent application Publication No. 2002/0129416 abandoned). The new variety 'Letitia Time Improved' has been asexually reproduced by vegetative cuttings in Chichester, West Sussex, United Kingdom and the distinguishing characteristics are retained through successive generations of asexual reproduction.

BRIEF SUMMARY OF THE INVENTION

'Letitia Time Improved' is a pot type of *Chrysanthemum* plant variety having large cream white single flowers and a light green disc.

Comparison with Female Parent

Plants of the new *Chrysanthemum* variety 'Letitia Time Improved' are dissimilar to the female parent 'Swell Time' in plant habit and growth rate. In side-by-side comparisons in Chichester, West Sussex, United Kingdom, under commercial practice, plants of the new *Chrsyanthemum* variety 'Letitia Time Improved' differed from plants of the female parent 'Swell Time' in the following characteristics:

1. The new variety 'Letitia Time Improved' produces cream white single flowers whereas the female parent 'Swell Time' produces lemon single flowers.
2. Plants of the new variety 'Letitia Time Improved' have larger and taller inflorescence than plants of the female parent 'Swell Time'.
3. Plants of the new variety 'Letitia Time Improved' have a slower response than plants of the female parent 'Swell Time'.

Comparison with Male Parent

Plants of the new *Chrsyanthemum* variety 'Letitia Time Improved' are dissimilar to the male parent 'Cool Time' in plant habit and growth rate. In side-by-side comparisons in Chichester, West Sussex, United Kingdom, under commercial practice, plants of the new *Chrsyanthemum* variety 'Letitia Time Improved' differed from plants of the male parent 'Cool Time' in the following characteristics:

1. The new variety 'Letitia Time Improved' produces cream white single flowers whereas the male parent 'Cool Time' produces white single flowers.
2. Plants of the new variety 'Letitia Time Improved' have a smaller vigor than plants of the male parent 'Cool Time'.

Comparison with 'Icey Isle'

Plants of the new *Chrysanthemum* variety 'Letitia Time Improved' are dissimilar to plants of the variety 'Icey Isle' (U.S. Plant Pat. No. 9,416) in plant habit and growth rate. However, in side-by-side comparisons in Chichester, West Sussex, United Kingdom, under commercial practice, plants of the new *Chrysanthemum* variety 'Letitia Time Improved' differed from plants of 'Icey Isle' in the following characteristics:

1. The new variety 'Letitia Time Improved' produces cream white single flowers whereas 'Icey Isle' produces white single flowers.
2. Plants of the new variety 'Letitia Time Improved' have smaller and shorter inflorescence than plants of 'Icey Isle'.
3. Plants of the new variety 'Letitia Time Improved' have a quicker response than plants of 'Icey Isle'.

BRIEF DESCRIPTION OF ILLUSTRATIONS

Typical specimens of the plant and flowers for the new *Chrysanthemum* variety 'Letitia Time Improved' are shown in the accompanying digital photograph. The colors shown are as true as possible within the usual limits of this kind of illustration.

FIG. 1 is a whole plant view of the new variety 'Letitia Time Improved' grown in a pot. The plant shown in the illustration is 56 days from the onset of Short Days.

DETAILED BOTANICAL DESCRIPTION

The following description of the new *Chrysanthemum* variety 'Letitia Time Improved' is of plants grown in a greenhouse in Chichester, West Sussex, United Kingdom, in the month of October. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 2,500 Lux. The plants respond well to the use of growth retardant, such as one B9 treatment at about 2 grams per liter. To produce a commercial product, the plants may be pinched once with the center bud removed. The typical container size for commercial growth is 1 liter. It has been observed that the shelf life of the new variety is about 28 days with a response time of about 7.5 weeks. The new variety is suitable for growth in a temperature range of 15° C. to 25° C.

The following description is with respect to a plant produced as pot *Chrysanthemum.* In the description of this new *Chrysanthemum* variety, color values have been taken from The Royal Horticultural Society Colour (R.H.S.C.C.).

Plant

Plant Type: Pot.
Habit: Upright and free branching.
Height (cm): 19.
Width (cm): 26.
Stem:
- *Length* (*cm*).—5.
- *Diameter* (*cm*).—0.6.
- *Texture.*—Slightly pubescent.
- *Color.*—138B.

Branching Characteristics: Upright and free branching.
Lateral Branches:
- *Length* (*cm*).—10.
- *Diameter* (*cm*).—0.4.
- *Texture.*—Slightly pubescent.

Number of Breaks from Pinch: 6.
Response Time: 52 days.
Vigor: Medium/Tall.
Shelf Life: 28 days.
Life of blooms: 28 days.
Disease (Susceptibility/Resistance observed): None observed to date.
Pest (Susceptibility/Resistance observed): None observed to date.
Drought and temperature (Susceptibility/Resistance observed): None observed to date.
Growth Retardant Type and Treatment: 3 applications of 2.5 gm/liter B9@ 2, 21 and 28 days after sticking unrooted cuttings.
The plants were grown for two weeks in Long Day conditions (20 hours of light) and then transferred to Short Day conditions (13 hours of dark).
Propagation:
- *Type.*—Vegetative propagation via stem cuttings.
- *Time to rooting.*—14 days with soil temperatures of 18° C.
- *Rooting habit.*—After 7 Long Days, the first roots emerge and form root primordia. In 14 Long Days, a complete root system is developed.

Foliage

Number of Leaves per Lateral Branch: 10.
Compound or Single: Single.
Arrangement of Leaves: Alternate.
- *Shape of leaf.*—Typically 5 lobed.
- *Size of leaf.*—Width (cm): 4 Length (cm): 6.
- *Leaf apex.*—Acute.
- *Base.*—Obtuse.
- *Attachment.*—Petioled.
- *Aspect.*—Slightly undulating.
- *Margin.*—Palmately lobed.
- *Surface characteristics.*—Top: Slightly pubescent. Bottom: Pubescent.

Petiole:
- *Color.*—137B.
- *Length* (*cm*).—2.5.
- *Diameter* (*cm*).—0.4.
- *Surface.*—Slightly pubescent.

Venation: Net, prominent lateral and mid-veins at underside.
- *Color.*—Upper side: 138B. Under side: 138B.

Color:
- *Mature leaf, upper side.*—137A; under side: 138A.
- *Young leaf, upper side.*—137A; under side: 138A.

Flower

Flower appearance: Matte.
Flower type: Single.
Flower form: Slightly cupped.
Flower shape: Circular.
Flowering habit: Cyme.
Number of blossoms per branch: 6.
Typical and observed flowering season: January to December.
Inflorescence form: Cyme.
*Depth of fully expanded blossoms* (*cm*).—1.8.
*Diameter of fully expanded blossoms* (*cm*).—8.
Phyllaries:
*Number.*—36.
*Color.*—137C.
*Length* (*cm*).—0.7.
*Width* (*cm*).—0.2.
*Texture/Appearance.*—Slightly pubescent.
Peduncle:
*Length* (*cm*).—10.
*Diameter* (*cm*).—0.4.
*Angle from stem* (*degrees*).—15.
*Color.*—138B.
*Surface.*—Slightly pubescent.
*Habit.*—Slightly undulating.
*Strength.*—Strong.
Pedicel:
*Length.*—terminal (cm): 3; lateral (cm): 3.5.
*Diameter* (*cm*).—0.2.
*Color.*—138B.
*Surface.*—Slightly pubescent.
*Habit.*—Straight.
*Strength.*—Moderately.
Ray florets:
*Form/Shape.*—Straight with parallel edges to the central mid vein.
*Texture/Appearance.*—Matte.
*Number per flower.*—24.
*Length* (*cm*).—3.5 Width (cm): 1.
*Apex.*—Rounded.
*Base.*—Tapered.
*Margin.*—Entire.
Disc florets:
*Form/Shape.*—Cylindric.
*Texture/Appearance.*—Shiny.
*Number per flower.*—200.
*Length* (*cm*).—0.6; Width (cm): 0.1.
*Diameter of disc* (*cm*).—1.5.
Fragrance: None.
Flower Bud (at onset of color):
*Length* (*cm*).—1.
*Diameter* (*cm*).—1.2.
*Form/Shape.*—Globular.
General flower color:
1. *Ray florets, upper side.*—Immature: 1C. Mature: 1D. Older/Fading: 155D.
2. *Ray florets, under side.*—Immature: 1C. Mature: 1D. Older/Fading: 155D.
3. *Disc florets.*—Immature: 144A. Mature: 144B. Older/Fading: 144C.
4. *Bud.*—1C.

Flower progression with age: There is no change with the flower form but the color does change from a lemon to cream white with age.

Reproductive Organs

Gynoecium present on Ray and Disc florets.
Ray florets per individual flower: Pistillate.
*Pistil number.*—24.
*Stigma color.*—154A.
*Stigma shape.*—Forked.
*Style color.*—154B.
*Style length* (*cm*).—0.3.
Disc florets per individual flower: Pistillate.
*Pistil number.*—200.
*Stigma color.*—154A.
*Stigma shape.*—Forked.
*Style color.*—154B.
*Style length* (*cm*).—0.3.
Androecium: Not observed.
Fruit and seeds: None observed.

What is claimed is:

1. A new and distinct variety of *Chrysanthemum* plant, substantially as described and illustrated herein.

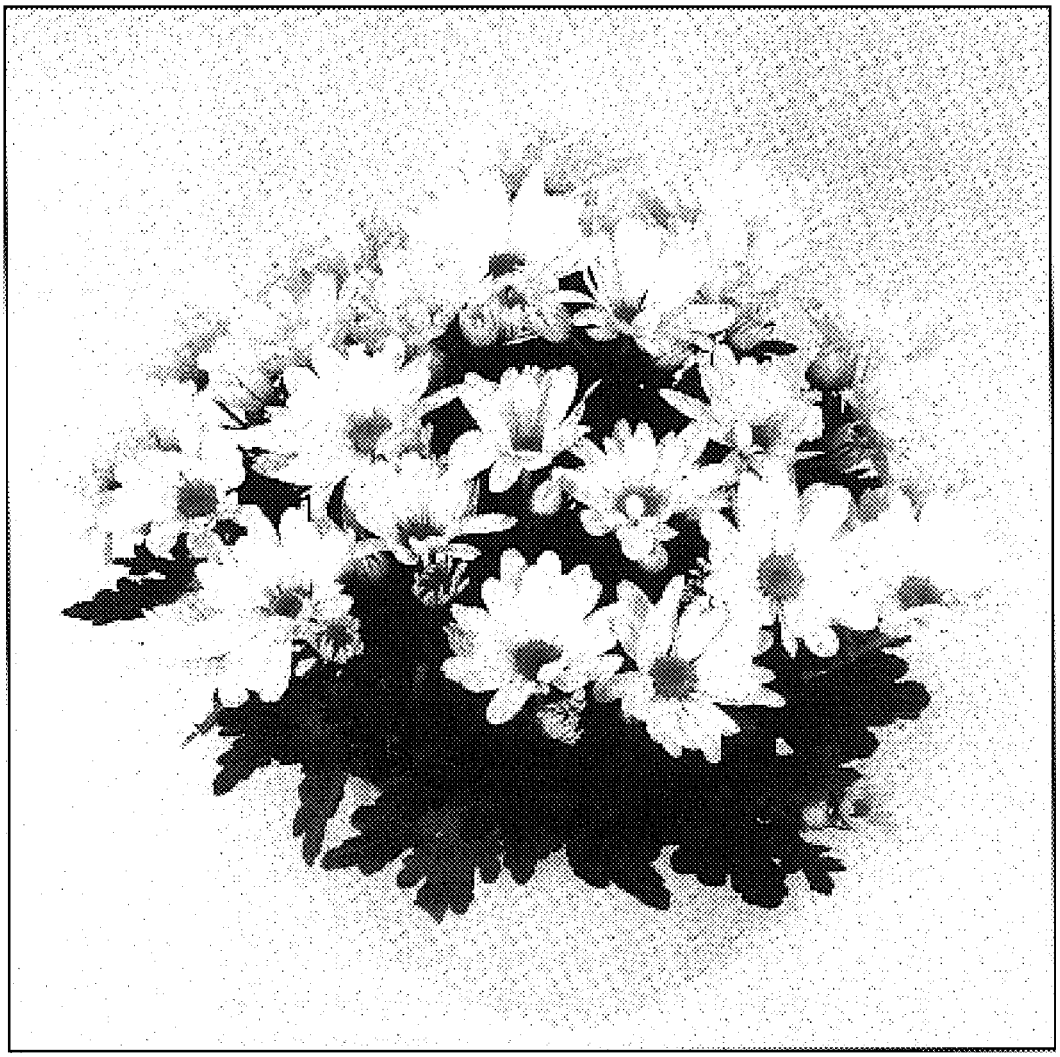

* * * * *